United States Patent [19]

Chang et al.

[11] 4,096,163

[45] Jun. 20, 1978

[54] CONVERSION OF SYNTHESIS GAS TO HYDROCARBON MIXTURES

[75] Inventors: Clarence D. Chang, Princeton; William H. Lang, Pennington, both of N.J.; Anthony J. Silvestri, Morrisville, Pa.; Robert L. Smith, Hopewell, N.J.

[73] Assignee: Mobil Oil Corporation, New York, N.Y.

[21] Appl. No.: 730,871

[22] Filed: Oct. 8, 1976

Related U.S. Application Data

[63] Continuation-in-part of Ser. No. 566,162, Apr. 8, 1975, abandoned, which is a continuation-in-part of Ser. No. 463,711, Apr. 24, 1974, abandoned.

[51] Int. Cl.$^2$ .............................................. C07C 1/04
[52] U.S. Cl. .................... 260/449 R; 260/449 M; 260/449.6 M; 260/449.6 R; 260/683 R; 252/455 Z
[58] Field of Search ........ 260/449 R, 449 M, 449.6 R, 260/449.6 M, 683 R

[56] References Cited

U.S. PATENT DOCUMENTS

| | | | |
|---|---|---|---|
| 1,834,621 | 12/1931 | Jaeger | 260/449.6 |
| 1,840,450 | 1/1932 | Jaeger et al. | 260/449.6 UX |
| 1,925,389 | 9/1933 | Jaeger | 260/449.6 |
| 2,754,314 | 7/1956 | McGrath | 260/449 R |
| 3,013,984 | 12/1961 | Breck | 252/455 Z |
| 3,013,990 | 12/1961 | Breck | 252/455 Z |
| 3,254,023 | 5/1966 | Miale et al. | 260/449 R X |
| 3,579,438 | 5/1971 | Cruse | 260/683 |
| 3,597,494 | 8/1971 | Bigache et al. | 260/683 R |
| 3,702,886 | 11/1972 | Argauer et al. | 423/328 |
| 3,709,979 | 1/1973 | Chu | 252/455 Z |
| 3,871,993 | 3/1975 | Morrison | 252/455 Z |
| 3,932,552 | 1/1976 | Starks | 260/683 R |
| 3,972,958 | 8/1976 | Garwood | 260/449 R |

FOREIGN PATENT DOCUMENTS

| | | | |
|---|---|---|---|
| 828,228 | 10/1975 | Belgium | 260/449 |
| 1,036,837 | 8/1958 | Germany | 260/449 R |
| 293,185 | 7/1928 | United Kingdom | 260/449.6 |
| 378,943 | 8/1952 | United Kingdom | 260/449 R |

OTHER PUBLICATIONS

Abdulahad et al., Brennstoff Chemie, 25, No. 4, (1972) 187–188.
Storch et al., Fischer Tropsch & Related Synthesis, John Wiley & Sons, New York, 1951, 428–436, 454–458.

*Primary Examiner*—Howard T. Mars
*Attorney, Agent, or Firm*—Charles A. Huggett; Michael G. Gilman

[57] ABSTRACT

Synthesis gas is contacted with an intimate mixture of a carbon monoxide hydrogen reduction catalyst, comprising a methanol synthesis catalyst in combination with a selective class of acidic crystalline aluminosilicate having a silica/alumina ratio greater than 12, a pore dimension greater than about 5 Angstroms to produce hydrocarbon mixtures useful in the manufacture of heating fuels, gasoline, aromatic hydrocarbons, and chemicals intermediates.

4 Claims, No Drawings

CONVERSION OF SYNTHESIS GAS TO HYDROCARBON MIXTURES

This application is a continuation-in-part of application Ser. No. 566,162 filed Apr. 8, 1975 and now abandoned which is a continuation-in-part of application Ser. No. 463,711, filed Apr. 24, 1974 now abandoned.

BACKGROUND OF THE INVENTION

1. Field of the Invention

This invention is concerned with an improved process for converting synthesis gas, i.e., mixtures of gaseous carbon oxides with hydrogen or hydrogen donors, to hydrocarbon mixtures. In one aspect, this invention is particularly concerned with a process for converting synthesis gas to hydrocarbon mixtures rich in aromatic hydrocarbons. In another aspect, this invention is concerned with a process for converting synthesis gas to hydrocarbon mixtures particularly rich in liquefiable petroleum gases such as propane. In still another aspect, this invention is concerned with providing novel catalysts for the conversion of synthesis gas to hydrocarbon mixtures.

2. Prior Art

Processes for the conversion of coal and other hydrocarbons such as natural gas to a gaseous mixture consisting essentially of hydrogen and carbon monoxide, or of hydrogen and carbon dioxide, or of hydrogen and carbon monoxide and carbon dioxide, are well known. Although various processes may be employed for the gasification, those of major importance depend either on the partial combustion of the fuel with an oxygen-containing gas or on the high temperature reaction of the fuel with steam, or on a combination of these two reactions. An excellent summary of the art of gas manufacture, including synthesis gas, from solid and liquid fuels, is given in Encyclopedia of Chemical Technology, Edited by Kirk-Othmer, Second Edition, Volume 10, pages 353-433, (1966), Interscience Publishers, New York, New York, the contents of which are herein incorporated by reference. The techniques for gasification of coal or other solid, liquid or gaseous feul are not considered to be per se inventive here.

It would be very desirable to be able to effectively convert synthesis gas, and thereby coal and natural gas, to highly valued hydrocarbons such as motor gasoline with high octane number, petrochemical feedstocks, liquefiable petroleum fuel gas, and aromatic hydrocarbons. It is well known that synthesis gas will undergo conversion to form reduction products of carbon monoxide, such as hydrocarbons, and/or oxygen containing compounds such as methanol at from about 300° to about 850° F under from about one to one thousand atmospheres pressure, over a fairly wide variety of catalysts. The Fischer-Tropsch process, for example, which has been most extensively studied, produces a range of liquid hydrocarbons, a portion of which have been used as low octane gasoline. The types of catalysts that have been studied for this and related processes include those based on metals, oxides or other compounds of iron, cobalt, nickel, ruthenium, thorium, rhodium and osmium. Methanol synthesis process, e.g. use catalyst based on metals or oxides of zinc and copper.

The wide range of catalysts and catalyst modifications disclosed in the art and an equally wide range of conversion conditions for the reduction of carbon monoxide by hydrogen provide considerable flexibility toward obtaining selected boiling-range products. Nonetheless, in spite of this flexibility, it has not proved possible to make such selections so as to produce liquid hydrocarbons in the gasoline boiling range which contain highly branched paraffins and substantial quantities of aromatic hydrocarbons, both of which are desired for high quality gasoline, or to selectively produce aromatic hydrocarbons particularly rich in the benzene to xylenes range. A review of the status of this art is given in "Carbon Monoxide-Hydrogen Reactions", Encyclopedia of Chemical Technology, Edited by Kirk-Othmer, Second Edition, Volume 4, pp. 446-488 and Volume 13, pages 370-398. Interscience Publishers, New York, N.Y., the text of which is incorporated herein by reference.

Recently it has been discovered that synthesis gas may be converted to oxygenated organic compounds and these then converted to higher hydrocarbons, particularly high octane gasoline, by catalytic contact of the synthesis gas with a carbon monoxide reduction catalyst followed by contacting the conversion products so produced with a special type of zeolite catalyst in a separate reaction zone. This two-stage conversion is described in copending U.S. patent application, Ser. No. 387,220, filed on Aug. 9, 1973.

It is an object of the present invention to provide an improved process for converting fossil fuels to a hydrocarbon mixture that contains large quantities of highly desirable constituents. It is a further object of this invention to provide a more efficient method for converting a mixture of gaseous carbon oxides and hydrogen to a mixture of hydrocarbons. It is a further object of this invention to provide an improved method for converting synthesis gas to a hydrocarbon mixture rich in aromatic hydrocarbons. It is a further object of this invention to provide a method for converting synthesis gas to petrochemicals feedstocks, including paraffins and olefins. It is a further object of this invention to provide an improved method for converting synthesis gas to propane fuel. It is a further object of this invention to provide novel catalysts for the conversion of synthesis gas.

BRIEF SUMMARY OF THE INVENTION

It has now been discovered that valuable hydrocarbon mixtures may be produced by reacting synthesis gas, i.e., mixtures of hydrogen gas with gaseous carbon oxides, or the equivalents of such mixtures, in the presence of certain heterogeneous catalysts comprising intimate mixtures of at least two components. The effective intimate mixtures, as will be more fully described hereinafter, are those in which a first component is selected from the class of inorganic substances that have catalytic activity for the reduction with hydrogen of carbon monoxide, and a second component is an acidic crystalline aluminosilicate of selected characteristics. Depending on the choice of components and the particular reaction condition, one may obtain substantial quantities of liquid mixtures which are rich in branched paraffins and aromatic hydrocarbons and eminently suited for making high octane gasoline or petrochemicals. Alternatively, one may select catalyst and operating conditions in such a manner, as will hereinafter be described, to produce normally gaseous hydrocarbons having at least one carbon-to-carbon bond as the predominant product. Such products have value as petrochemical feedstocks, and for the manufacture of liquefiable petroleum fuel. The catalyst mixtures produce highly desirable products with good selectivity and in many cases produce them with extraordinarily high conversion per pass. With a methanol synthesis catalyst of the zinc-copper type of inorganic substance as the reducing component, synthesis gas conversion rate is increased and large proportions of hydrocarbons having at least one carbon-to-carbon bond are obtained instead of methanol alone. Furthermore, when the preferred class of acidic crystalline aluminosilicate component herein defined is used in the intimate mixture, the catalytic activity is sustained for unusually long periods of time and the aromatic hydrocarbons, when produced, are rich in toluene and xylenes.

DETAILED DESCRIPTION AND PREFERRED EMBODIMENTS

Synthesis gas for use in this invention consists of a mixture of hydrogen gas with gaseous carbon oxides including carbon monoxide and carbon dioxide. By way of illustration, a typical purified synthesis gas will have the composition, on a water-free basis, in volume percentages, as follows: hydrogen, 51; carbon monoxide, 40; carbon dioxide, 4; methane, 1; and nitrogen, 4.

The synthesis gas may be prepared from fossil fuels by any of the known methods, including such in situ gasification processes as the underground partial combustion of coal and petroleum deposits. The term fossil fuels, as used herein, is intended to include anthracite and bituminous coal, lignite, crude petroleum, shale oil, oil from tar sands, natural gas, as well as fuels derived from simple physical separations or more profound transformations of these materials, including coked coal, petroleum coke, gas oil, residua from petroleum distillation, and two or more of any of the foregoing materials in combination. Other carbonaceous fuels such as peat, wood and cellulosic waste materials also may be used.

The raw synthesis gas produced from fossil fuels will contain various impurities such as particulates, sulfur, and metal carbonyl compounds, and will be characterized by a hydrogen-to-carbon oxides ratio which will depend on the fossil fuel and the particular gasification technology utilized. In general, it is desirable for the efficiency of subsequent conversion steps to purify the raw synthesis gas by the removal of impurities. Techniques for such purification are known and are not part of this invention. It is preferred to adjust the hydrogen-to-carbon oxides volume ratio to be within the range of from 0.2 to 6.0 prior to use in this invention. Should the purified synthesis gas be excessively rich in carbon oxides, it may be brought within the preferred range by the well known water-gas shift reaction. On the other hand, should the synthesis gas be excessively rich in hydrogen, it may be adjusted into the preferred range by the addition of carbon dioxide or carbon monoxide. Purified synthesis gas adjusted to contain a volume ratio of hydrogen-to-carbon oxides of from 0.2 to 6.0 will be referred to as adjusted synthesis gas.

It is contemplated that the synthesis gas for use in this invention includes art-recognized equivalents to the already described mixtures of hydrogen gas with gaseous carbon oxides. Mixtures of carbon monoxide and steam, for example, or of carbon dioxide and hydrogen, to provide adjusted synthesis gas by in situ reaction, are contemplated.

The heterogeneous catalysts of this invention comprise at least two components intimately mixed, and in which one component is selected from the class of inorganic substances that have catalytic activity for the reduction by hydrogen of carbon monoxide, and in which the other component is a class of acidic crystalline aluminosilicate characterized by a pore dimension greater than about 5 Angstroms, a silica-to-alumina ratio of at least 12 and a constraint index within the range of 1 to 12.

The inorganic substance or component characterized by catalytic activity for the reduction by hydrogen of carbon monoxide may be selected from any of the art-recognized methanol synthesis catalysts for producing hydrocarbons, oxygenated products, or mixtures thereof, from synthesis gas. Broadly, these include those recognized as zinc and/or copper methanol synthesis catalysts, and variants thereof. Commercial methanol synthesis catalysts comprising metals or oxides of zinc together with chromia, or of zinc and copper together with chromia or alumina, or known modifications of these, are included. In fact, synthesis gas will undergo conversion to form reduction products of carbon monoxide, such as alcohols and hydrocarbons at temperatures in the range of from about 300° to about 850° F, and pressures in the range of from about 1 to 100 atmospheres pressure, over a fairly wide variety of catalysts.

The inorganic component that has catalytic activity for the reduction of carbon monoxide with hydrogen such as zinc and/or copper active component should in all cases constitute from 0.05% to 99% by weight, and preferably from 0.1% to 80% by weight of the active components of the intimate mixture. The carbon monoxide reducing component may be furnished as elemental metal or as corresponding metal compound.

The acidic crystalline aluminosilicate component of the heterogeneous catalyst is characterized by a pore dimension greater than about 5 Angstroms, i.e., it is capable of sorbing paraffins having a single methyl branch as well as normal paraffins, and it has a silica-to-alumina ratio of at least 12. Zeolite A, for example, with a silica-to-alumina ratio of 2.0 is not useful in this invention, and it has no pore dimension greater than about 5 Angstroms.

The crystalline aluminosilicates herein referred to, also known as zeolites, constitute an unusual class of natural and synthetic minerals. They are characterized by having a rigid crystalline framework structure composed of an assembly of silicon and aluminum atoms, each surrounded by a tetrahedron of shared oxygen atoms, and a precisely defined pore structure. Exchangeable cations are present in the pores.

The catalysts referred to herein utilize members of a special class of zeolites exhibiting some unusual properties. These zeolites induce profound transformations of aliphatic hydrocarbons to aromatic hydrocarbons in commercially desirable yields and are generally highly effective in alkylation, isomerization, disproportionation and other reactions involving aromatic hydrocarbons. Although they have unusually low alumina contents, i.e. high silica to alumina ratios, they are very active even with silica to alumina ratios exceeding 30. This activity is surprising since catalytic activity of zeolites is generally attributed to framework aluminum atoms and cations associated with these aluminum atoms. These zeolites retain their crystallinity for long periods in spite of the presence of steam even at high temperatures which induce irreversible collapse of the crystal framework of other zeolites, e.g. of the X and A type. Furthermore, carbonaceous deposits, when formed, may be removed by burning at higher than usual temperatures to restore activity. In many environments the zeolites of this class exhibit very low coke forming capability, conducive to very long times on stream between burning regenerations.

An important characteristic of the crystal structure of this class of zeolites is that it provides constrained access to, and egress from, the intra-crystalline free space by virtue of having a pore dimension greater than about 5 Angstroms and pore windows of about a size such as would be provided by 10-membered rings of oxygen atoms. It is to be understood, of course, that these rings are those formed by the regular disposition of the tetrahedra making up the anionic framework of the crystalline aluminosilicate, the oxygen atoms themselves being bonded to the silicon or aluminum atoms at the centers of the tetrahedra. Briefly, the preferred zeolites useful in type B catalysts in this invention possess, in combination: a silica to alumina ratio of at least about 12; and a structure providing constrained access to the crystalline free space.

The silica to alumina ratio referred to may be determined by conventional analysis. This ratio is meant to represent, as closely as possible, the ratio in the rigid anionic framework of the zeolite crystal and to exclude aluminum in the binder or in cationic or other form within the channels. Although zeolites with a silica to alumina ratio of at least 12 are useful it is preferred to use zeolites having higher ratios of at least about 30. Such zeolites, after activation, acquire an intracrystalline sorption capacity for normal hexane which is greater than that for water, i.e., they exhibit "hydrophobic" properties. It is believed that this hydrophobic character is advantageous in the present invention.

The zeolites useful as catalysts in this invention freely sorb normal hexane and have a pore dimension greater than about 5 Angstroms. In addition, their structure must provide constrained access to some larger molecules. It is sometimes possible to judge from a known crystal structure whether such constrained access exists. For example, if the only pore windows in a crystal are formed by 8-membered rings oxygen atoms, then access by molecules of larger cross-section than normal hexane is substantially excluded and the zeolite is not of the desired type. Zeolites with windows of 10-membered rings are preferred, although excessive puckering or pore blockage may render these zeolites substantially ineffective. Zeolites with windows of twelve-membered rings do not generally appear to offer sufficient constraint to produce the advantageous conversions desired in the instant invention, although structures can be conceived, due to pore blockage or other cause, that may be operative.

Rather than attempt to judge from crystal structure whether or not a zeolite possesses the necessary constrained access, a simple determination of the "constraint index" may be made by continuously passing a mixture of equal weight of normal hexane and 3-methylpentane over a small sample, approximately 1 gram or less, of zeolite at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 1000° F for at least 15 minutes. The zeolite is then flushed with helium and the temperature adjusted between 550° and 950° F to give an overall conversion between 10% and 60%. The mixture of hydrocarbons is passed at 1 liquid hourly space velocity (i.e., 1 volume of liquid hydrocarbon per volume of catalyst per hour) over the zeolite with a helium dilution to give a helium to total hydrocarbon mole ratio of 4:1. After 20 minutes on stream, a sample of the effluent is taken and analyzed, most conveniently by gas chromatography, to determine the fraction remaining unchanged for each of the two hydrocarbons.

The "constraint index" is calculated as follows:

$$\text{Constraint Index} = \frac{\log_{10}(\text{fraction of n-hexane remaining})}{\log_{10}(\text{fraction of 3-methylpentane remaining})}$$

The constraint index approximates the ratio of the cracking rate constants for the two hydrocarbons. Catalysts suitable for the present invention are those which employ a zeolite having a constraint index from 1.0 to 12.0. Constraint Index (CI) values for some typical zeolites including some not within the scope of this invention are:

| CAS | C.I. |
|---|---|
| Erionite | 38 |
| ZSM-5 | 8.3 |
| ZSM-11 | 8.7 |
| ZSM-35 | 6.0 |
| TMA Offretite | 3.7 |
| ZSM-38 | 2.0 |
| ZSM-12 | 2 |
| Beta | 0.6 |
| ZSM-4 | 0.5 |
| Acid Mordenite | 0.5 |
| REY | 0.4 |
| Amorphous Silica-alumina | 0.6 |

The above-described Constraint Index is an important and even critical, definition of those zeolites which are useful to catalyze the instant process. The very nature of this parameter and the recited technique by which it is determined, however, admit of the possibility that a given zeolite can be tested under somewhat different conditions and thereby have different constraint indexes. Constraint Index seems to vary somewhat with severity of operation (conversion). Therefore, it will be appreciated that it may be possible to so select test conditions to establish multiple constraint indexes for a particular given zeolite which may be both inside and outside the above defined range of 1 to 12.

Thus, it should be understood that the parameter and property "Constraint Index" as such value is used herein is an inclusive rather than an exclusive value. That is, a zeolite when tested by any combination of conditions within the testing definition set forth herein above to have a constraint index of 1 to 12 is intended to be included in the instant catalyst definition regardless that the same identical zeolite tested under other defined conditions may give a constraint index value outside of 1 to 12.

The class of zeolites defined herein is exemplified by ZSM-5, ZSM-11, ZSM-12, ZSM-35 and ZSM-38, and other similar materials. Recently issued U.S. Pat. No. 3,702,886 describing and claiming ZSM-5 is incorporated herein by reference.

ZSM-11 is more particularly described in U.S. Pat. No. 3,709,979, the entire contents of which are incorporated herein by reference.

ZSM-12 is more particularly described in U.S. Pat. No. 3,832,449, the entire contents of which are incorporated herein by reference.

The subject of ZSM-35 is described in U.S. application Ser. No. 528,061 filed Nov. 29, 1974 now U.S. Pat.

No. 4,016,245. The subject of ZSM-38 is described in U.S. application Ser. No. 528,060 filed Nov. 29, 1974 now U.S. Pat. No. 4,046,859.

The specific zeolites described, when prepared in the presence of organic cations, are substantially catalytically inactive, possibly because the intracrystalline free space is occupied by organic cations from the forming solution. They may be activated by heating in an inert atmosphere at 1000° F for one hour, for example, followed by base exchange with ammonium salts followed by calcination at 1000° F in air. The presence of organic cations in the forming solution may not be absolutely essential to the formation of this special type zeolite; however, the presence of these cations does appear to favor the formation of this special type of zeolite. More generally, it is desirable to activate this type zeolite by base exchange with ammonium salts followed by calcination in air at about 1000° F for from about 15 minutes to about 24 hours.

Natural zeolites may sometimes be converted to this type zeolite by various activation procedures and other treatments such as base exchange, steaming, alumina extraction and calcination, alone or in combinations. Natural minerals which may be so treated include ferrierite, brewsterite, stilbite, dachiardite, epistilbite, heulandite and clinoptilolite. The preferred crystalline aluminosilicates are ZSM-5, ZSM-11, ZSM-12, ZSM-35 and ZSM-38, with ZSM-5 particularly preferred.

The zeolites used as catalysts in this invention may be in the hydrogen form or they may be base exchanged or impregnated to contain ammonium or a metal cation complement. It is desirable to calcine the zeolite after base exchange. The metal cations that may be present include any of the cations of the metals of Groups I through VIII of the periodic table. However, in the case of Group IA metals, the cation content should in no case be so large as to substantially eliminate the activity of the zeolite for the catalysis being employed in the instant invention. For example, a completely sodium exchanged H-ZSM-5 appears to be largely inactive for shape selective conversions required in the present invention.

In a preferred aspect of this invention, the zeolites useful as catalysts herein are selected as those having a crystal framework density, in the dry hydrogen form, of not substantially below about 1.6 grams per cubic centimeter. It has been found that zeolites which satisfy all three of these criteria are most desired. Therefore, the preferred catalysts of this invention are those comprising zeolite having a constraint index as defined above of about 1 to 12, a silica to alumina ratio of at least about 12 and a dried crystal density of not substantially less than about 1.6 gram per cubic centimeter. The dry density for known structures may be calculated from the number of silicon plus aluminum atoms per 1000 cubic Angstroms, as given, e.g., on page 19 of the article on Zeolite Structure by W. M. Meier. This paper, the entire contents of which are incorporated herein by reference, is included in "Proceedings of the Conference Molecular Sieves, London, April, 1967", published by the Society of Chemical Industry, London, 1968. When the crystal structure is unknown, the crystal framework density may be determined by classical pyknometer techniques. For example, it may be determined by immersing the dry hydrogen form of the zeolite in an organic solvent which is not sorbed by the crystal. It is possible that the unusual sustained activity and stability of this class of zeolites is associated with its high crystal anionic framework density of not less than about 1.6 grams per cubic centimeter. This high density of course must be associated with a relatively small amount of free space within the crystal, which might be expected to result in more stable structures. This free space, however, seems to be important as the locus of catalytic activity.

Crystal framework densities of some typical zeolites including some which are not within the purview of this invention are:

| Zeolite | Void Volume | Framework Density |
|---|---|---|
| Ferrierite | 0.28 cc/cc | 1.76 g/cc |
| Mordenite | .28 | 1.7 |
| ZSM-5,-11 | .29 | 1.79 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

The heterogeneous catalysts may be prepared in various ways. The two components may be separately prepared in the form of catalyst particles such as pellets or extrudates, for example, and simply mixed in the required proportions. The particle size of the individual component particles may be quite small, for example, from about 20 to about 150 microns, when intended for use in fluid bed operation; or they may be as large as up to about ½ inch for fixed bed operation. Or, the two components may be mixed as powders and formed into pellets or extrudate, each pellet containing both components in substantially the required proportions. Binders such as clays may be added to the mixture. Alternatively, the component that has catalytic activity for the reduction of carbon monoxide may be formed on the acidic crystalline aluminosilicate component by conventional means such as impregnation of that solid with salt solutions of the desired metals, followed by drying and calcination. Base exchange of the acidic crystalline aluminosilicate component also may be used in some selected cases to effect the introduction of part or all of the carbon monoxide reduction component. Other means for forming the intimate mixture may be used, such as: precipitation of the carbon monoxide reduction component in the presence of the acidic crystalline aluminosilicate; or electroless deposition of metal on the zeolite; or deposition of metal from the vapor phase. Various combinations of the above preparative methods will be obvious to those skilled in the art of catalyst preparation. It should be cautioned, however, to avoid techniques likely to reduce the crystallinity of the acidic crystalline aluminosilicate.

It will be recognized from the foregoing description that the heterogeneous catalysts, i.e., the above-described intimate mixtures, used in the process of this invention, may have varying degrees of intimacy. At one extreme, when using ½ inch pellets of the carbon monoxide reducing component mixed with ½ inch pellets of the acidic crystalline aluminosilicate, substantially all locations within at least one of the components will be within not more than about ½ inch of some of the other component, regardless of the proportions in which the two components are used. With different sized pellets, e.g., ½ inch and ¼ inch, again substantially all locations within at least one of the components will be within not more than about ½ inch of the other component. These examples illustrate the lower end of the degree of intimacy required for the practice of this invention. At the other extreme, one may ball mill together acid crystalline aluminosilicate particles of about 0.1 micron particle size with colloidal zinc oxide of similar particle size followed by pelletization. For this case, substantially all the locations within at least one of the components will be within not more than about 0.1 micron of some of the other component. This exemplifies about the highest degree of intimacy that is practical. The degree of intimacy of the physical mixture may also be expressed as the minimum distance of separation of the central points located within the particles of the two components. This will, on average, be represented by one-half the sum of the average particle size for the two components. Thus, for the foregoing example illustrating the highest degree of intimacy, the centers of the particles of either of the two components will be separated from the nearest particle of the other component by an average distance of at least about 0.1 micron. The degree of intimacy of the heterogeneous catalyst is largely determined by its method of preparation, but it may be independently verified by physical methods such as visual observations, examination in an ordinary microscope or with an electron microscope, or by electron microprobe analysis.

In the process of this invention, synthesis gas is contacted with the heterogeneous catalyst at a temperature in the range of from about 400° to about 1000° F, preferably from about 500° to about 850° F, at a pressure in the range of from about 1 to about 1000 atmospheres, preferably from about 3 to about 200 atmospheres, and at a volume hourly space velocity in the range of from about 500 to about 50,000 volumes of gas, at standard temperature and pressure per volume of catalyst, or equivalent contact time if a fluidized bed is used. The heterogeneous catalyst may be contained as a fixed bed, or a fluidized bed may be used. The product stream containing hydrocarbons, unreacted gases and steam may be cooled and the hydrocarbons recovered by any of the techniques known in the art, which techniques do not constitute part of this invention. The recovered hydrocarbons may be further separated by distillation or other means to recover one or more products such as high octane gasoline, propane fuel, benzene, toluene, xylenes, or other aromatic hydrocarbons.

EXAMPLE 1

A ZnO supported on $Al_2O_3$ was obtained from a commercial source and was used as the carbon monoxide reducing component. It contained 24% by weight of ZnO. HZSM-5 was used as the acidic crystalline aluminosilicate component.

The heterogeneous composite catalyst was prepared by ballmilling together four parts of the HZSM-5 to one part of the $ZnO/Al_2O_3$ catalyst, followed by pelletizing. Two runs were carried out, both at 600° F, 750 psia, and with a mixture of hydrogen and carbon monoxide having a $H_2/CO$ ratio of 4. The first run used the $ZnO/Al_2O_3$ catalyst alone, while the second run employed the composite catalyst containing both the $ZnO/Al_2O_3$ and HZSM-5 catalysts.

The results are shown in Table 1.

Table 1

| Catalyst | (D) $ZnO/Al_2O_3$ Alone | (E) 20% $ZnO/Al_2O_3$ plus 80% HZSM-5 Composite |
|---|---|---|
| Contact Time - seconds (at reaction conditions) | 25 | 25 |
| Conversion, wt.% | | |
| CO | 32.0 | 6.7 |
| $H_2$ | 5.4 | 3.4 |
| Wt. % hydrocarbons in total reaction effluent | 0.2 | 1.0 |
| Hydrocarbon Distribution (wt.%) | | |
| Methane | 100.0 | 11.4 |
| $C_2$-$C_4$ hydrocarbons | — | 42.9 |
| $C_5$+ | — | 45.7 |
| | 100.0 | 100.0 |
| Aromatics in $C_5$+(wt.%) | None | 71.8 |

EXAMPLE 2

A methanol synthesis catalyst was prepared containing the following percentages by weight; copper - 54.55, zinc - 27:27, chromium - 9.09, and lanthanum - 9.09 on an oxygen-free basis. A composite catalyst was then prepared from equal parts of this component and HZSM-5, using 5% graphite as a binder. Two runs were made, each at 600° F, 750 psia, using as a feed a mixture of hydrogen and carbon monoxide with a $H_2/CO$ ratio of 2 and are summarized in Table 2.

Table 2

| Catalyst | (F) Methanol Type Alone | (G) Methanol Type plus HZSM-5 Composite |
|---|---|---|
| Space Velocity on Methanol Catalyst Component (cc of synthesis gas/g. of methanol catalyst/hour) | 5825 | 6764 |
| CO Conversion wt.% | 24 | 34 |
| Wt.% in Water-Free Product | | |
| Methane | 0.7 | 1.1 |
| $C_2$-$C_4$ Hydrocarbons | 1.0 | 5.7 |
| $C_5$+ Hydrocarbons | 1.0 | 1.8 |
| | 2.7 | 8.6 |

As shown, the contact times (reciprocal of space velocity) relative to the methanol catalyst component are very similar in the two runs; being slightly lower with the composite catalyst.

The composite catalyst shows a much greater production of hydrocarbons, particularly hydrocarbons higher in carbon number than methane, than the carbon monoxide reducing component by itself.

EXAMPLE 3

The catalysts used in this example comprised a mixture of ZSM-5 alumina extrudate (65/35 ratio) with a copper methanol synthesis catalyst used in Runs 912-1 thru 5. In Runs 912-1 and 2, the volume ratio of ZSM-5/Cu synthesis catalyst was 2.9/2 and in Runs 912-3 to 5, the volume ratio of ZSM-5/Cu synthesis catalyst was 4/1. The operating conditions employed and results obtained in the respective Runs are identified in Table 3 below.

Table 3

| Catalyst (14–25 Mesh) | HZSM-5/CuMethanol Synthesis Catalyst | | | | |
|---|---|---|---|---|---|
| $H_2/CO$ Ratio | 2/1 | | 2/1 | | |
| Vol. Ratio, HZSM-5/Syn.Cat. | 2.92 | | 4/1 | | |
| Pressure, psig. | 200 | 400 | 750 | | |
| GHSV | 2440 | 2600 | 1210 | | |
| WHSV | 1.56 | 1.66 | 0.86 | | |
| Temp. °F. Bed Setting | 600 | 650 | 600 | | |
| Average | 604 | 659 | 614 | 612 | 608 |
| Hot Spot | 607 | 663 | 623 | 618 | 611 |
| Run Time, Hours | 19½ | 20 | 20 | 24 | 20 |
| Accum. Time, Days | 0.8 | 1.6 | 1.2 | 2.2 | 3.0 |
| CO Conversion, wt.% | 31 | 45 | 80 | 70 | 55 |
| $H_2$ Conversion, wt.% | 8 | 14 | 38 | 28 | 19 |
| %Wt. C converted to: | | | | | |
| $CO_2$ | 49 | 45 | 45 | 46 | 46 |
| Hydrocarbon | 51 | 55 | 55 | 54 | 54 |
| Hydrocarbon composition, wt.% | | | | | |
| $C_1$ | 3 | 3 | 4 | 4 | 3 |
| $C_2$ | 14 | 13 | 21 | 18 | 16 |
| $C_3$ | 29 | 23 | 21 | 19 | 19 |
| $C_4$ | 21 | 17 | 17 | 19 | 19 |
| $C_5$ | 14 | 14 | 10 | 12 | 13 |
| $C_6+$ | 19 | 20 | 27 | 28 | 30 |
| | 100 | 100 | 100 | 100 | 100 |
| Aromatics in $C_6+$, wt.% | 19 | 37 | 34 | 31 | 32 |
| $C_{10}$ Aromatics in $C_6+$, wt.% | 9 | 24 | 32 | 29 | 28 |
| Tetra-methyl benzenes | 8 | 22 | 32 | 29 | 27 |
| Durene | 3 | 12 | 17 | 16 | 15 |
| Run No. | 912-1 | -2 | 913-3 | -4 | -5 |

Water phase separated contained high percentages of methanol. The presence of methanol contributes to the formation of durene.

EXAMPLE 4

The catalyst used in this example comprised a mixture of ZnO, $Al_2O_3$ and HZSM-5 in a weight ratio of 12/38/50 respectively. The operating conditions employed and the results obtained are identified in Table 4 below. It will be particularly observed that high yields of ethane and propane were obtained.

Table 4

| Run No. LPA 111A ($ZnO/Al_2O_3$/HZSM-5) | |
|---|---|
| T = 800° F | |
| P = 1200 psig. | |
| $H_2/CO$ = 1 | |
| WHSV = 1.8 | |
| Conversion % | |
| CO | 32.7 |
| $H_2$ | 29.7 |
| Hydrocarbons, wt.% | |
| Methane | 15.2 |
| Ethane | 34.3 |
| Ethylene | 0.1 |
| Propane | 26.3 |
| Propylene | 0.1 |
| Butanes | 6.4 |
| Butenes | — |
| $C_5+$ PON | 2.1 |
| Aromatics | 15.5 |
| | 100.0 |

EXAMPLE 5

In this example, synthesis gas (syngas) was reacted at 700° F, 2000 GHSV, 10 atm. and 50 atm. over a catalyst comprising equal weights of a (copper, zinc, chromium, lanthanum oxide methanol synthesis catalyst) and HZSM-5 crystalline zeolite ball milled together to < 20 μ and then pelletized. The hydrocarbon product obtained consisted entirely of $C_1$–$C_6$ paraffins as shown in Table 5, instead of some anticipated aromatics.

Table 5
SYNGAS CONVERSION TO LIGHT PARAFFINS
700° F, 2000 GHSV, $H_2/CO$ = 2

| Run No. | MHC3D | MHC3C |
|---|---|---|
| PRESSURE, ATM. | 10 | 50 |
| CONVERSION, Wt.% | | |
| $H_2$ | 10.4 | 24.8 |
| CO | 23.5 | 53.3 |
| TOTAL PRODUCT, WT.% | | |
| Hydrocarbons | 6.05 | 15.49 |
| Oxygenates | 0.03 | 0.02 |
| $H_2$ | 11.2 | 9.4 |
| CO | 66.9 | 40.9 |
| $CO_2$ | 15.9 | 34.1 |
| $H_2O$ | tr. | tr. |
| HYDROCARBON DISTRIBUTION Wt.% | | |
| Methane | 4.8 | 11.6 |
| Ethane | 66.1 | 36.8 |
| Ethylene | — | — |
| Propane | 10.6 | 27.1 |
| Propylene | — | — |
| i-Butane | 6.1 | 7.1 |
| n-Butane | — | 3.8 |
| Butenes | — | — |
| i-Pentane | 7.8 | 6.4 |
| n-Pentane | — | 1.1 |
| Pentenes | — | — |
| $C_6$ | 4.6 | 6.1 |
| $C_7+$ | — | — |
| Aromatics | — | — |

EXAMPLE 6

A zinc oxide/aluminum oxide ($Al_2O_3$) methanol synthesis catalyst of low olefin hydrogenation activity and low methanol synthesis activity was combined in equal weights with a HZSM-5 crystalline zeolite and then ball milled together and pelletized. Synthesis gas was passed in contact with this catalyst mixture under the conditions identified in Table 6 below. Table 6 shows the results of comparative experiments using $ZnO/Al_2O_3$ alone and the $ZnO/Al_2O_3$/HZSM-5 dual function catalyst mixture. It can be seen from these data that although conversions to hydrocarbons were low, the product of the ZSM-5 containing catalyst was highly aromatic. The $Zn/Al_2O_3$ catalyst alone yielded traces of methane as the sole hydrocarbon product.

Table 6
SYNGAS CONVERSION TO AROMATICS
600° F, 50 atm., 1000 GHSV, $H_2/CO = 4$

| Run No. | MHC 7A | MHC 8A |
|---|---|---|
| Catalyst | $ZnO/Al_2O_3$ | $ZnO/Al_2O_3$ + HZSM-5 |
| Conversion, wt.% | | |
| $H_2$ | 5.4 | 3.4 |
| CO | 32.0 | 6.7 |
| Total Product, wt.% | | |
| Hydrocarbons | 0.15 | 0.96 |
| Oxygenates | 12.29[a] | 0.04 |
| $H_2$ | 21.21 | 21.46 |
| CO | 52.91 | 72.56 |
| $CO_2$ | 5.44 | 4.97 |
| $H_2O$ | tr. | tr |
| Hydrocarbon Distribution Wt.% | | |
| Methane | 100.00 | 11.4 |
| Ethane | — | 9.0 |
| Ethylene | — | — |
| Propane | — | 29.0 |
| Propylene | — | — |
| i-Butane | — | 4.9 |
| n-Butane | — | — |
| Butenes | — | — |
| i-Pentane | — | 8.0 |
| n-Pentane | — | — |
| Pentenes | — | — |
| $C_6 P+O$ | — | 2.7 |
| $C_7 P+O$ | — | 2.2 |
| Benzene | — | — |
| Toluene | — | 1.2 |
| Ethylbenzene | — | — |
| Xylenes | — | 5.8 |
| $A_9$ | — | 16.7[b] |
| $A_{10}$ | — | 9.1 |
| $A_{11}$ | — | — |
| Total $C_5+$ | 0 | 45.7 |
| Total aromatics | 0 | 32.8 |

[a] 18% methanol, 82% dimethyl ether
[b] 76% 1, 2, 4 trimethylbenzene

EXAMPLE 7

A Zn-exchanged ZSM-5 catalyst was used for conversion of synthesis gas. The catalyst comprised 1.1 wt. % Zn, 64.3 wt. % HZSM-5 and 34.6 wt. % $Al_2O_3$.

Synthesis gas ($H_2/CO = 1$) was passed at a rate of 75 standard cc/min. over 3.5 grams of said catalyst at 250 psig and 700° F. Conversion per pass of carbon monoxide was 8.1%. The hydrocarbon product consisted of 38.1 wt. % methane, 36.4 wt. % ethane, 11.9 wt. % propane, 5.7 wt. % isobutane and 7.9 wt. % isopentane.

The method of the present invention contemplates in one aspect the formation of desired olefin product. To accomplish this end it is proposed to effect the conversion of synthesis gases to ethylene for example in two stages. In the first stage, the synthesis gas is converted to light paraffins, mainly $C_2-C_4$ paraffins by judicious selection of temperature and pressure conditions in the presence of a dual component or dual function catalyst comprising a methanol synthesis catalyst comprising zinc and/or copper in combination with a zeolite from the class of zeolites represented by HZSM-5. In this combination a particular catalyst mixture is selected which will form desired paraffin rich product in a first stage and the paraffins thus formed are then pyrolyzed or thermally cracked in a second stage at a temperature in the range of about 1300° F to about 1800° F with or without the presence of added steam, to form an olefinic product high in ethylene concentration. Recycle of unreacted paraffin to the second stage of the combination operation is contemplated. It is recognized that steam pyrolysis of paraffins to form ethylene is known in the art. However the preparation of particularly desired paraffin feed for such use derives novelty from the particular combination of the present invention to accomplish that end. It is of interest to note that in the absence of fine grinding, mixtures of the copper and/or chromium containing methanol synthesis catalysts with HZSM-5 catalyst particles tend to produce mainly methanol and aromatics containing durene from synthesis gas. A particular advantage attributed to the combination operation of this invention is found in the combination providing high selectivities to ethane and propane product achieved with the dual component catalyst suitable for the purpose. These hydrocarbons are particularly preferred feeds for pyrolysis to ethylene as shown by the following table taken from Nelson, "Petroleum Refinery Engineering". The table lists the ultimate yields of ethylene achieved in commercial practice for different feed compositions.

| Feed | Wt.% | Conversion % per pass |
|---|---|---|
| From ethane | 74–75 | 60 |
| From propane | 42–43 | 85 |
| From propylene | 26–27 | — |
| From butane | 38–39* | 85–90 |
| From kerosene or gas oil | 22–23 | 58** |

*When recycling propylene
**Based on wt.% production of butanes and lighter.

Having thus generally described the invention and discussed specific embodiments in support thereof, it is to be understood that no undue restrictions are to be imposed by reason thereof except as defined by the following claims.

We claim:

1. In the process of converting synthesis gas, comprising carbon monoxide and hydrogen, to a hydrocarbon product by contacting such at about 450 to 1000° F with a catalyst comprising as a first component a metal carbon monoxide reduction catalyst and as a second component an acidic crystalline aluminosilicate zeolite having a silica to alumina ratio of at least 12 and a constraint index of about 1 to 12; the improvement which comprises utilizing as said carbon monoxide reducing catalyst component a methanol synthesis catalyst comprising copper or chromium containing catalysts or mixtures thereof in a finely ground form and thereby converting said synthesis gas to substantially only $C_1 - C_6$ paraffins composed mainly of $C_2 - C_4$ paraffins.

2. The method of claim 1 wherein said crystalline aluminosilicate is selected from a class of crystalline zeolites comprising ZSM-5, ZSM-11, ZSM-12, ZSM-35 and ZSM-38.

3. The method of claim 1 wherein the synthesis gas hydrogen to carbon oxides volume ratio is maintained within the range of from 0.2 to 6.0

4. The method of claim 1 wherein said methanol synthesis catalyst comprises:
 metals or oxides of zinc together with chromia;
 metals or oxides of zinc and copper together with chromia or alumina; or
 metals or oxides of zinc, copper, chromium and lanthanum.

* * * * *